United States Patent [19]
Becker et al.

[11] Patent Number: 5,337,601
[45] Date of Patent: Aug. 16, 1994

[54] METHOD AND APPARATUS FOR MEASURING PRESSURE IN A SEALED WELL USING A DIFFERENTIAL TRANSDUCER

[75] Inventors: William L. Becker; William J. Kuestner, both of Laramie, Wyo.

[73] Assignee: In-Situ, Inc., Laramie, Wyo.

[21] Appl. No.: 5,623

[22] Filed: Jan. 19, 1993

[51] Int. Cl.$^5$ .................. E21B 47/00; G01N 15/08
[52] U.S. Cl. .......................... 73/155; 73/38; 166/250
[58] Field of Search ............ 73/155, 38, 152, 153; 166/250; 175/48

[56] References Cited

U.S. PATENT DOCUMENTS

| | | | |
|---|---|---|---|
| 2,972,050 | 2/1961 | Allen | 250/43.5 |
| 3,350,931 | 11/1967 | Johnson et al. | 73/152 |
| 3,955,411 | 5/1976 | Lawson, Jr. | 73/155 |
| 4,083,228 | 4/1978 | Turner et al. | 73/38 |
| 4,096,737 | 6/1978 | Schuh | 73/46 |
| 4,125,163 | 11/1978 | Fitzpatrick | 166/250 |
| 4,142,411 | 3/1979 | Deal | 73/155 |
| 4,252,015 | 2/1981 | Harbon et al. | 73/151 |
| 4,423,625 | 1/1984 | Bostic, III et al. | 166/250 |
| 4,458,754 | 7/1984 | Barnes, Jr. et al. | 166/250 |
| 4,790,378 | 12/1988 | Montgomery et al. | 166/250 |
| 4,802,359 | 2/1989 | Patrice | 73/155 |
| 4,938,060 | 7/1990 | Sizer et al. | 73/151 |
| 4,972,705 | 11/1990 | Fryer et al. | 73/155 |
| 4,986,120 | 1/1991 | Yanagisawa et al. | 166/250 |
| 5,197,541 | 3/1993 | Hess et al. | 166/267 |

Primary Examiner—Hezron E. Williams
Assistant Examiner—George Dombroske
Attorney, Agent, or Firm—Sheridan Ross & McIntosh

[57] ABSTRACT

A system and method are disclosed for measuring pressure in a sealed well using a differential transducer. A differential transducer is employed in a number of applications to measure either the pressure in the upper portion of a well or the level of liquid contained in the well. In each application, the back side of the differential transducer is vented to the same pressure as is present in the upper portion of the well. In one embodiment, the present invention is used to determine information relating to the liquid level in a well during a soil vapor extraction procedure. The information is then used to control a pump which maintains a desired liquid level in the well. In another embodiment, the present invention is used to determine information relating to the liquid level in a well during a pneumatic slug test. The information is then used to determine how quickly the well can recover from changes in pressure. In an alternate embodiment, the present invention is used to measure the effects of a vacuum applied to one well on another well located some distance away. The measured effect is then used to calculate the permeability of the soil between the wells.

12 Claims, 5 Drawing Sheets

METHOD AND APPARATUS FOR MEASURING PRESSURE IN A SEALED WELL USING A DIFFERENTIAL TRANSDUCER

FIELD OF THE INVENTION

The present invention relates generally to using a differential transducer to measure the pressure present in a sealed well.

BACKGROUND OF THE INVENTION

Three general types of transducers are presently available for measuring pressure: differential, sealed, and absolute. The differential transducer (also called a gauge transducer) measures the difference between pressures applied to what are known as the "front" and "back" sides of its sensor. The sensor consists of a resistor network such as a Wheatstone bridge disposed on a diaphragm such that when pressure is applied to either side of the sensor the diaphragm is deformed, thus changing the resistance of the network. When different pressures are applied to either side of the diaphragm, the change in resistance in the network can be correlated to the difference in pressures applied to the front and back of the sensor.

The sealed transducer works on the same principle as the differential transducer except that the back of the transducer is sealed such that there is a constant pressure applied to the back of the diaphragm. Thus the sealed transducer will produce signals indicative of the difference between whatever pressure is applied to the front of the sensor and the constant pressure applied to the back.

The absolute transducer is a special type of sealed transducer wherein the constant pressure applied to the back of the transducer is zero. In other words, the back of the transducer is sealed with a hard vacuum. Thus, the absolute transducer will produce signals indicative of whatever pressure is applied to the front of the sensor relative to the vacuum.

The most commonly employed of these transducers in the measurement of pressure in a well is the differential transducer. For a number of years, differential transducers have been used to measure the level of a liquid in an unsealed well. This is a relatively simple measurement which entails lowering the differential transducer to a point below the surface of the liquid in the well, venting the back side of the transducer to atmospheric pressure outside of the well, and connecting the resistor network disposed on the diaphragm of the transducer to a data analyzer. The front side of the transducer then measures the pressure due to the column of liquid above the transducer plus the atmospheric pressure which pushes down on the surface of the liquid. By venting the back side of the transducer to conditions outside of the well, the effect of atmospheric pressure is negated and the transducer sends signals to the data analyzer indicative of the pressure caused by the column of liquid above the differential transducer. Since the depth to which the transducer was lowered is known, the data analyzer can then determine the level of liquid in the well.

If the same test were performed with an absolute or sealed transducer, the effect of atmospheric pressure on the surface of the liquid would not be taken into account, and an inaccurate level reading would result. It would also be inaccurate to merely program the data analyzer to subtract what is traditionally thought of as atmospheric pressure from the pressure read by an absolute transducer. This would not account for barometric changes in the atmosphere which could significantly affect results in a long-term test. Thus, differential transducers have traditionally been employed when measuring the level of liquid in an unsealed well. In fact, differential transducers are the most commonly used type of transducer in a variety of procedures because of their ability to compensate for changes in atmospheric pressure.

Recently, however, procedures have been developed which require a well to be sealed air-tight and an artificial pressure to be created in the well. When differential transducers have been used in these new procedures to measure pressure inside of the well, inaccurate readings have been produced. Since the pressure on the surface of the liquid is no longer the same as the pressure in the atmosphere, when the back side of the differential transducer is vented to the atmosphere, the pressure on the surface of the liquid is no longer canceled out. Thus, the signals produced by the transducer are no longer indicative of only the pressure caused by the column of water above the transducer.

One example of a procedure in which it is necessary to create an artificial pressure within a well is "soil vapor extraction." Soil vapor extraction refers to a method of removing contaminants from the soil by lowering the pressure in a well which is situated in or near the contaminated soil. If contaminants, such as gasoline for example, become trapped in soil a certain depth beneath the ground and above the table of groundwater, the contaminants can be removed through a well dug through the area of contamination to the groundwater table. When the well is sealed and a vacuum applied to it in order to lower the pressure, contaminants in the soil will volatilize and move into the well in vapor form. Once in the well, the vapor contaminants are removed by the vacuum and disposed of properly. However, when the vacuum is applied to the well, the water from the groundwater table tends to rise, and if the water rises to the level of the contaminants, the contaminants will not volatilize and will remain trapped in the soil. The well is therefore provided with a pump which can be used to remove enough water to keep the water level in the well below the level of the contaminants. In order to use the pump effectively, the level of the water in the well must be known at any given time.

When a differential transducer with its back side vented to the atmosphere has been used to measure the water level, the readings have been found to be in error for the reasons outlined above. Therefore, an incorrect water level is maintained. Absolute transducers have been used to obviate these errors, however, two absolute transducers are then required for each well. If a large number of wells are being measured at any one time, the use of two absolute transducers per well could require a significant investment. In addition, since most users already own differential transducers which can be used in other procedures, the use of absolute transducers is even less cost-effective.

Another procedure for which a well is sealed and an artificial pressure applied is a "pneumatic slug test." A slug test measures how fast water will move through an aquifer by either increasing or decreasing the amount of water in the well and timing how long it takes for the well to return to its original level. For years this test was performed using an unsealed well by either pumping water out of the well or adding water to the well and waiting for the well to recover to its original level. There are problems associated with each of these methods. Namely, if water is removed and the well is contaminated, then how to dispose of the contaminated water can be a problem. Alternatively, if water is added and the well is pristine, then there is a risk that the added water will contaminate the well.

Therefore, recently, technology has been developed to perform the slug test pneumatically, without adding or removing any water. In a pneumatic slug test the well is sealed, and the pressure in the well is then raised or lowered. This causes the water level in the well to drop or rise accordingly. The artificial pressure is then removed, and the time it takes for the water in the well to recover to its original level is measured. This avoids the potential problems of disposal and contamination. However, in order to perform this test, it is necessary to be able to accurately measure the level of the water in the well. It has been discovered that when using a differential transducer with its back side vented to the atmosphere to measure the water level when the artificial pressure is applied, inaccuracies occur for the reasons outlined above.

Another test which requires that a well be sealed and an artificial pressure applied is known as a "soil permeability test." This test measures the permeability of soil by testing how well air can pass through it. A soil permeability test is usually performed prior to a soil vapor extraction procedure in order to determine if soil vapor extraction is a viable method for cleaning up a contaminated plot of soil. Obviously, soil which is mostly made up of clay will not be as permeable as more granular soil. If the soil is not permeable enough, the contaminants in the soil are less likely to volatilize and another method of soil cleansing may be more effective.

A soil permeability test is performed using a plurality of wells. First, an extraction well is sealed and a pressure is applied to it. Then one or more monitoring wells near the extraction well are created and sealed. The pressure is measured in each monitoring well to gauge the effect of the pressure applied to the extraction well. In order to correlate the pressure changes in the monitoring wells to the permeability of soil between the wells, it is necessary to measure the true pressure being applied to the extraction well. The use of a differential transducer to measure the pressure applied to the extraction well is hampered in that if a vacuum is applied to an extraction well in which a differential transducer is suspended above the water level, the differential transducer will malfunction, because the diaphragm will be deformed in the wrong direction. The data analyzer will read an open circuit in the resistor network and no measurement will be possible. Absolute transducers which are designed to measure negative pressures (pressures below atmospheric) could be used, however, as discussed above, the use of absolute transducers is not cost effective given that they cannot be employed in all tests.

SUMMARY OF THE INVENTION

Accordingly, the present invention provides a system for measuring the pressure in a sealed well which obviates the problems of the prior art outlined above. The present invention allows multiple procedures which necessitate introducing an artificial procedure to sealed wells to be performed using only one differential transducer per well.

The present invention includes a differential transducer for measuring the pressure present at a particular location within a sealed well, means for creating a desired pressure in the upper portion of the well, and means for providing the same pressure to the back of the differential transducer. The present invention may also be provided with a data analyzer for receiving signals from the differential transducer indicating a sensed pressure. Also, a junction vent box may be employed to operatively interconnect the differential transducer with both the data analyzer and the means for creating a desired pressure. The junction vent box permits the back of the differential transducer to be connected through a channel in the transducer cable to the means for creating the desired pressure. The junction vent box also permits the electrical components of the differential transducer to be connected to the data analyzer through the transducer cable without splitting the transducer cable and destroying the integrity of the system.

In one embodiment the present invention is used in a soil vapor extraction procedure. In this case a pump is provided to remove liquid from the well, and the differential transducer is lowered to a point below the surface of the liquid in the sealed well. The transducer cable is connected to the junction vent box which interconnects a data analyzer to the differential transducer. A vacuum system is attached to the top of the well and creates a desired pressure in the upper portion of the well. The vacuum system is also connected to the junction vent box and applies the same desired pressure to the back of the differential transducer through a channel in the transducer cable. The pressure on the front of the transducer is then equal to the pressure created by the vacuum system plus the pressure due to the column of liquid above the transducer. However, since the pressure created by the vacuum system is also applied to the back of the differential transducer, the pressure created by the vacuum system sensed on the front of the differential transducer is canceled out. Thus, the differential transducer sends signals to the data analyzer representative of only the pressure due to the column of liquid above the differential transducer. Since the cross-sectional area of the well and the length of the transducer cable are known, the data analyzer can then determine the level of the liquid in the well. Thus, as the pressure in the well is lowered by the vacuum system in order to volatilize contaminants in the soil, the level can be controlled by pumping liquid out of the well dependent on the information provided by the data analyzer.

In another embodiment, the present invention is used during a pneumatic slug test. In this case, the apparatus are connected as in the soil vapor extraction procedure with the exception that no water pump is necessary. In the pneumatic slug test, the differential transducer again sends signals to the data analyzer through the junction vent box indicative of the pressure due to the column of liquid above the differential transducer.

In an alternate embodiment, the present invention is used to perform a soil permeability test. In this embodiment, the differential transducer is placed outside of the well, and the vacuum system is not directly connected to the junction vent box. Instead, a conduit is provided to operatively connect the junction vent box to the top of the well. Thus, the junction vent box is provided with the same pressure as the top of the well, and that pressure is again applied to the back of the differential transducer. The differential transducer then transmits signals to the data analyzer indicative of the difference between the atmospheric pressure sensed on the front of the differential transducer and the applied pressure present in the upper portion of the well. Peripheral monitoring wells are then provided to measure the effect of the applied pressure on air flow through the soil.

Other advantages and characteristics of the invention will become apparent in the following description of the invention given with reference to accompanying drawings.

DETAILED DESCRIPTION

Figure 1:
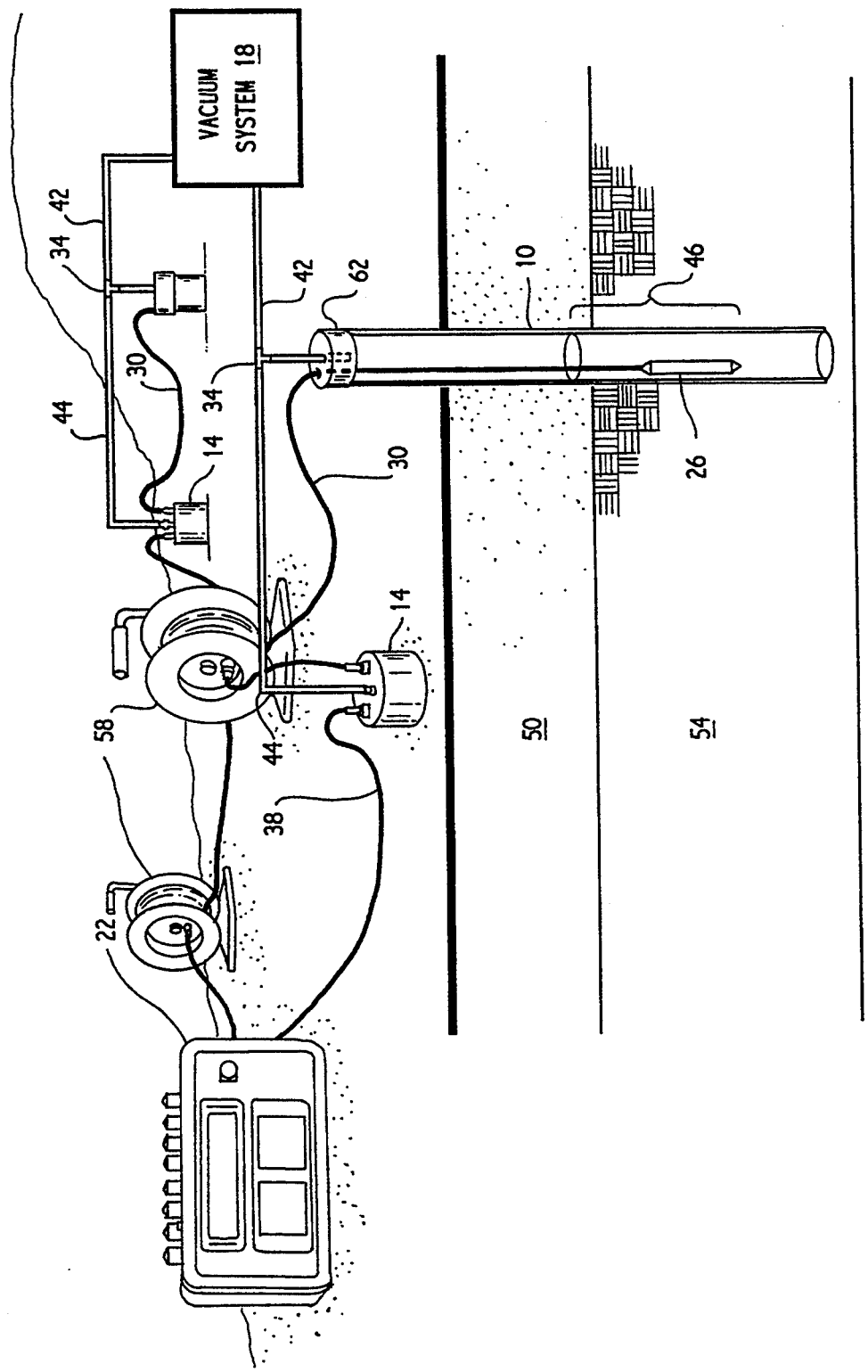
FIG. 1 is a schematic view of the present invention being used to measure the level of fluid in a well.

FIG. 1 shows an example of how the system of the present invention can be configured to measure the level of a fluid in a well. An extraction well 10 extends through the vadose level of soil 50 and into the groundwater table 54. The extraction well 10 is sealed with well cap 62, and a differential transducer 26 is suspended by transducer cable 30 at a level beneath the surface of the water in the extraction well 10. Transducer cable 30 also operatively interconnects differential transducer 26 with a junction vent box 14 through cable reel 58. Extraction well 10 is operatively interconnected with vacuum system 18 through tubing means 42. Vacuum system 18 is also operatively interconnected to junction vent box 14 through tubing means 42 and 44. Tee 34 serves to connect tubing means 42 and 44 to extraction well 10. A data analyzer 22 is also operatively connected to junction vent box 14 by cable 38.

The level of the water in extraction well 10 is then measured as follows. Vacuum system 18 creates a desired pressure in the upper portion of extraction well 10 through tubing means 42 and tee 34. The same pressure created by vacuum system 18 is supplied to junction vent box 14 through tubing means 44. Junction vent box 14 then applies the same pressure to the back of differential transducer 26 through transducer cable 30. Differential transducer 26 senses a pressure on its front side due to the sum of pressures created by vacuum system 18 and the column of water 46 above differential transducer 26. The height of the column of water 46 above differential transducer 26 is known as the "head." As discussed in the background section above, differential transducer 26 produces signals indicative of the difference in pressures applied to its front and back sides. In this case, the pressure created by vacuum system 18 is canceled out on either side of the differential transducer 26. Thus, differential transducer 26 will produce electrical signals indicative of the pressure caused solely by head 46. The electrical signals produced by differential transducer 26 are transmitted through transducer cable 30 and cable reel 58 to junction vent box 14. Junction vent box 14 then transmits the signals from differential transducer 26 to cable 38 which is connected to data analyzer 22. Data analyzer 22 then decodes the signals and determines the head 46. Given that the depth to which the differential transducer 26 was lowered is known, data analyzer 22 can then calculate the level of water in extraction well 10.

Figure 2:
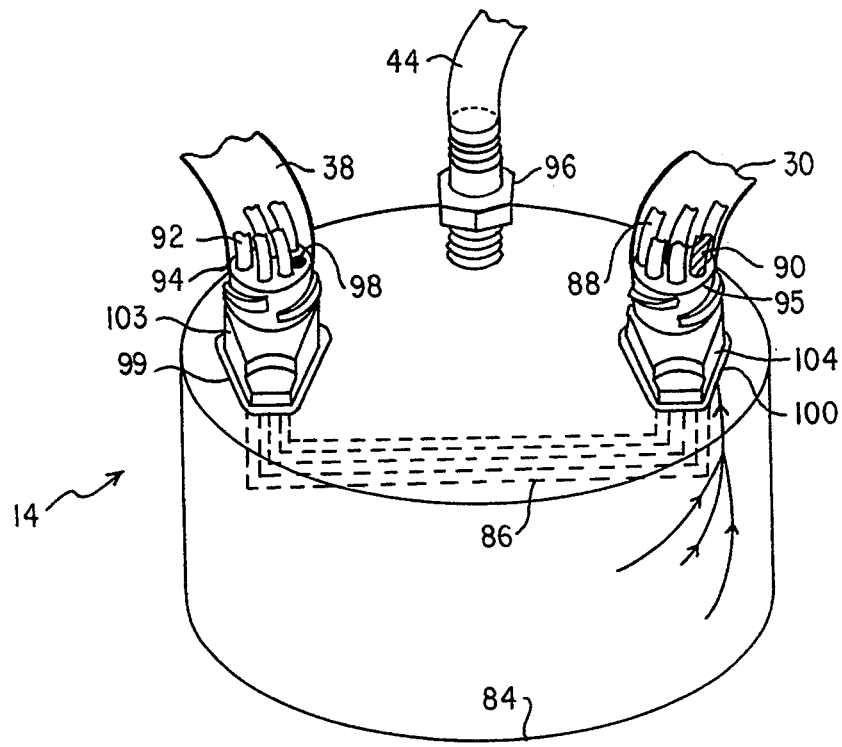
FIG. 2 is a detailed view of the junction vent box which can be used with the present invention.

With reference to FIG. 2, the operation of the junction vent box 14 will now be described in greater detail. Junction vent box 14 comprises a cylindrical housing 84 which encloses a cavity and has three openings in its upper wall. Two of the openings are provided with androgynous connectors 103 and 104 which receive data analyzer cable 38 and transducer cable 30 respectively. O-ring seals 94 and 95 seal the connection between cables 38 and 30 with their respective connectors 103 and 104. Flat rubber gaskets 99 and 100 are positioned to seal the connection of connectors 103 and 104 to junction vent box housing 84. The other opening in the upper wall of housing 84 is provided with a connector 96 to receive tubing 44 which is operatively interconnected to vacuum system 18. The cavity enclosed by housing 84 is pressurized by vacuum system 18 through tubing 44. The pressure in the cavity is then transmitted by transducer cable 30 through vent tube 90 to the back of differential transducer 26. In applications such as the pneumatic slug test which lasts only a few minutes, it is imperative that vent tube 90 be of sufficient diameter to allow the system to respond quickly to changes in pressure. It has been found that an inner diameter of 0.075 inches is a sufficient size of vent tube 90. Androgynous connectors 103 and 104 are provided with a plurality of apertures. One of the apertures in each seal is operable to receive a vent tube. However, the connector 103 which receives data analyzer cable 38 is provided with a plug 98 in order to seal the aperture for receiving a vent tube. The other apertures in connectors 103 and 104 receive electrical conductors 92 and 88 respectively. Electrical conductors 88 contained in transducer cable 30, transmit electrical signals from differential transducer 26 to junction vent box 14. Junction vent box 14 includes permanent electrical connections 86 between connectors 103 and 104. Electrical connections 86 can be wires or soldered connections and are operable to transmit electrical signals from electrical conductors 88 to electrical conductors 92. Thereby the electrical signals from differential transducer 26 are transmitted through transducer cable 30 to junction vent box 14 and through cable 38 to data analyzer 22.

Figure 3:
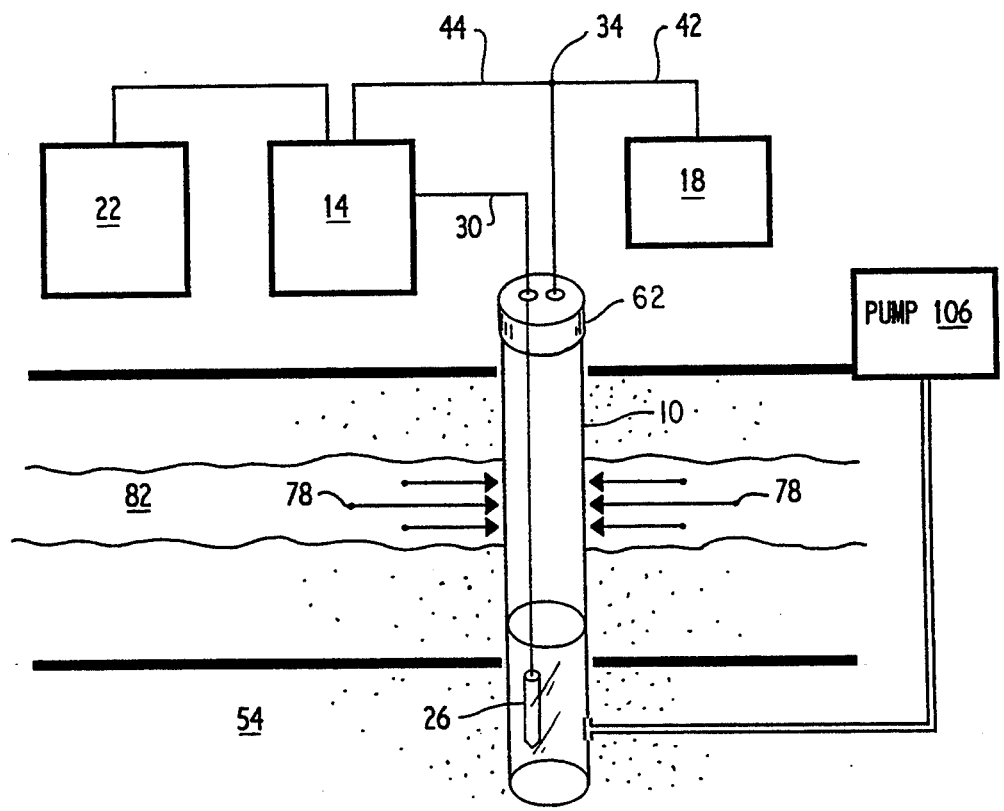
FIG. 3 is a schematic view of the present invention being used to perform soil vapor extraction.

Reference will now be made to FIG. 3 which depicts the present invention as configured for a soil vapor extraction procedure. Contaminants 78 are trapped in a contaminated layer of soil 82. As described in the background section above, in order to volatilize contaminants 78, the pressure in extraction well 10 must be lowered by vacuum system 18. However, when this occurs, the level of water in extraction well 10 tends to rise. If the level of water in extraction well 10 rises to the layer of contaminated soil 82, contaminants 78 will not volatilize and move into extraction well 10. A pump 106 is therefore provided to keep the level of water in the extraction well 10 below the contaminated layer 82. In order to effectively control pump 106, it is necessary to be able to measure the level of the water in extraction well 10 accurately (usually within inches). Differential transducer 26 is used to do so as described with reference to FIG. 1. Thus, as the pressure is lowered in extraction well 10 and the water level is maintained below the contaminated layer 82, contaminants 78 volatilize and enter extraction well 10 where they are removed in vapor form by vacuum system 18.

Figure 4A:
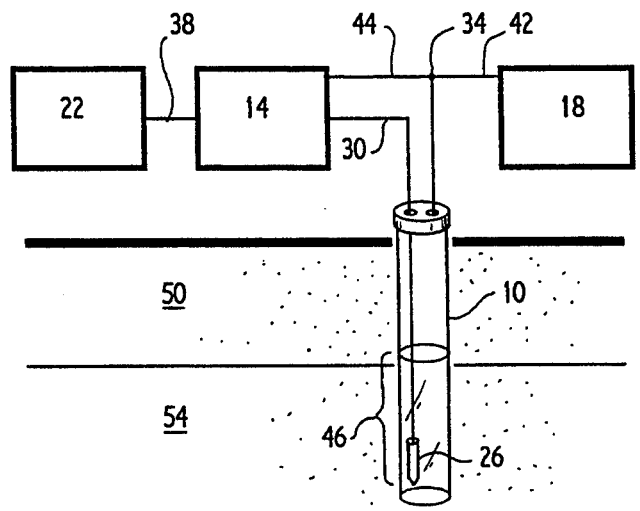
FIGS. 4a–4c are schematic views of the present invention being used to perform a pneumatic slug test.
Figure 4B:
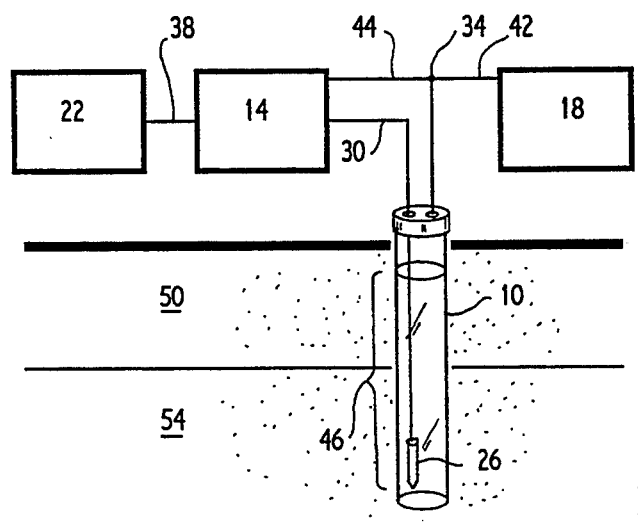
Figure 4C:
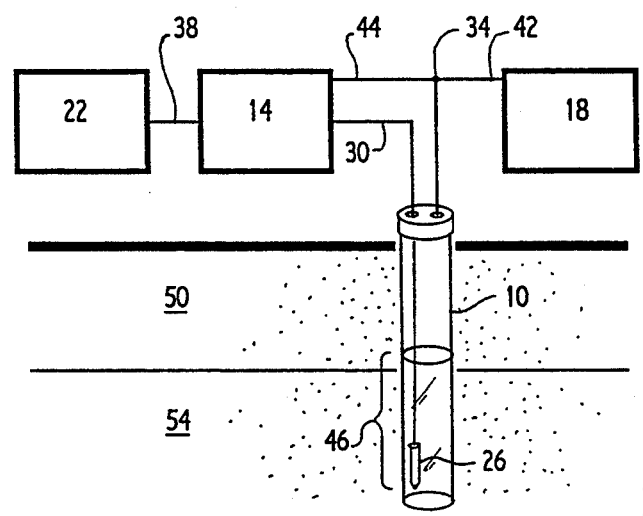

FIGS. 4a–4c illustrate another embodiment of the present invention as used in a pneumatic slug test. As discussed above, a pneumatic slug test measures how fast water will move through an aquifer by varying the pressure either to increase or decrease the amount of water in the well, and timing how long it takes for the well to return to its original level. In the example depicted, the aquifer is the groundwater table 54. FIG. 4a depicts the present invention when vacuum system 18 applies a first pressure to the upper portion of extraction well 10. FIG. 4b depicts the system of the present invention when vacuum system 18 lowers the pressure in extraction well 10 in order to make the water level rise. When vacuum system 18 reapplies the first pressure to extraction well 10, the water level will return to its original level as depicted in FIG. 4c.

Alternatively, the pneumatic slug test can begin with the vacuum system 18 disconnected from the well 10 which would then be at atmospheric pressure. Then an artificial pressure is applied to raise or lower the level of water in the well 10. Once the water in the well 10 reaches a desired level, vacuum system 18 is again disconnected, and the water is allowed to return to its original level at atmospheric pressure.

Throughout this test, in either embodiment, differential transducer 26 provides signals to data analyzer 22 indicative of the water level in extraction well 10 as described above with reference to FIG. 1. Data analyzer 22 is also provided with a timing mechanism such that it can measure the time it takes for the level of water in extraction well 10 to change from the level depicted in FIG. 4b to its original level as shown in FIG. 4c when the first pressure is reapplied. The difference in the level of water in extraction well 10 as depicted in FIGS. 4b and 4c can then easily be determined. The rate at which water moves through the groundwater table 54 can therefore also be calculated.

Figure 5:
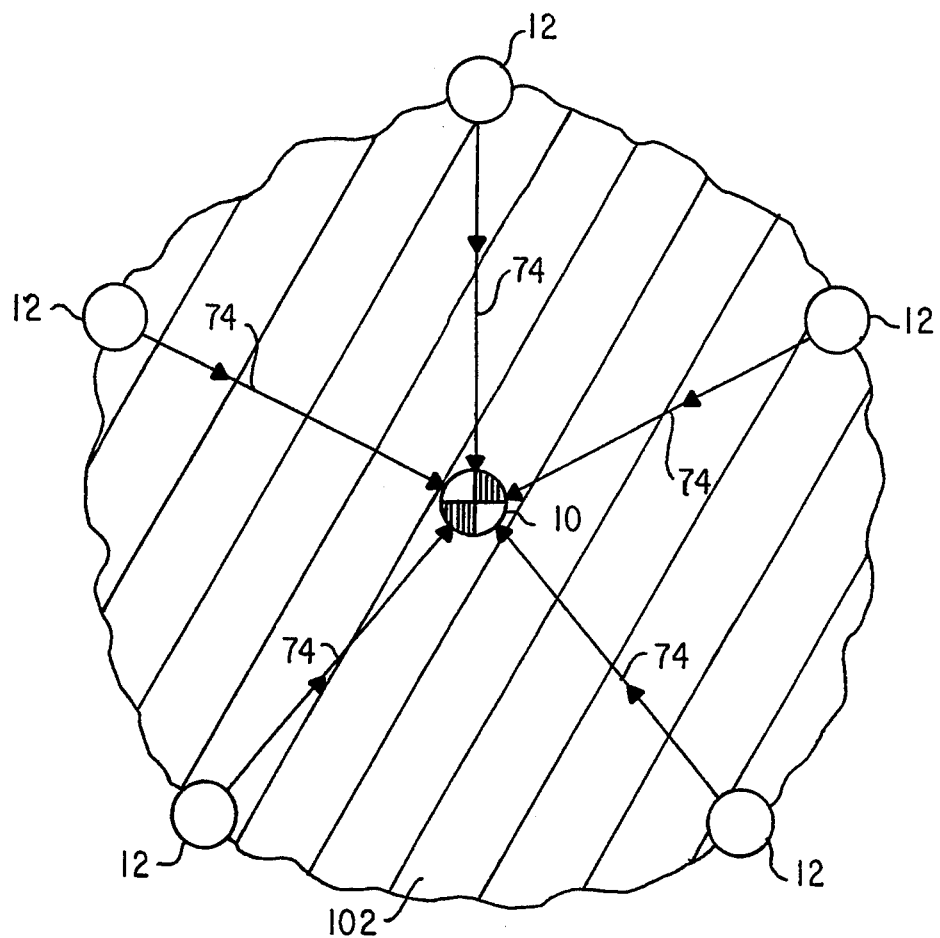
FIG. 5 is a schematic top view of air flow during a soil permeability test.
Figure 6:
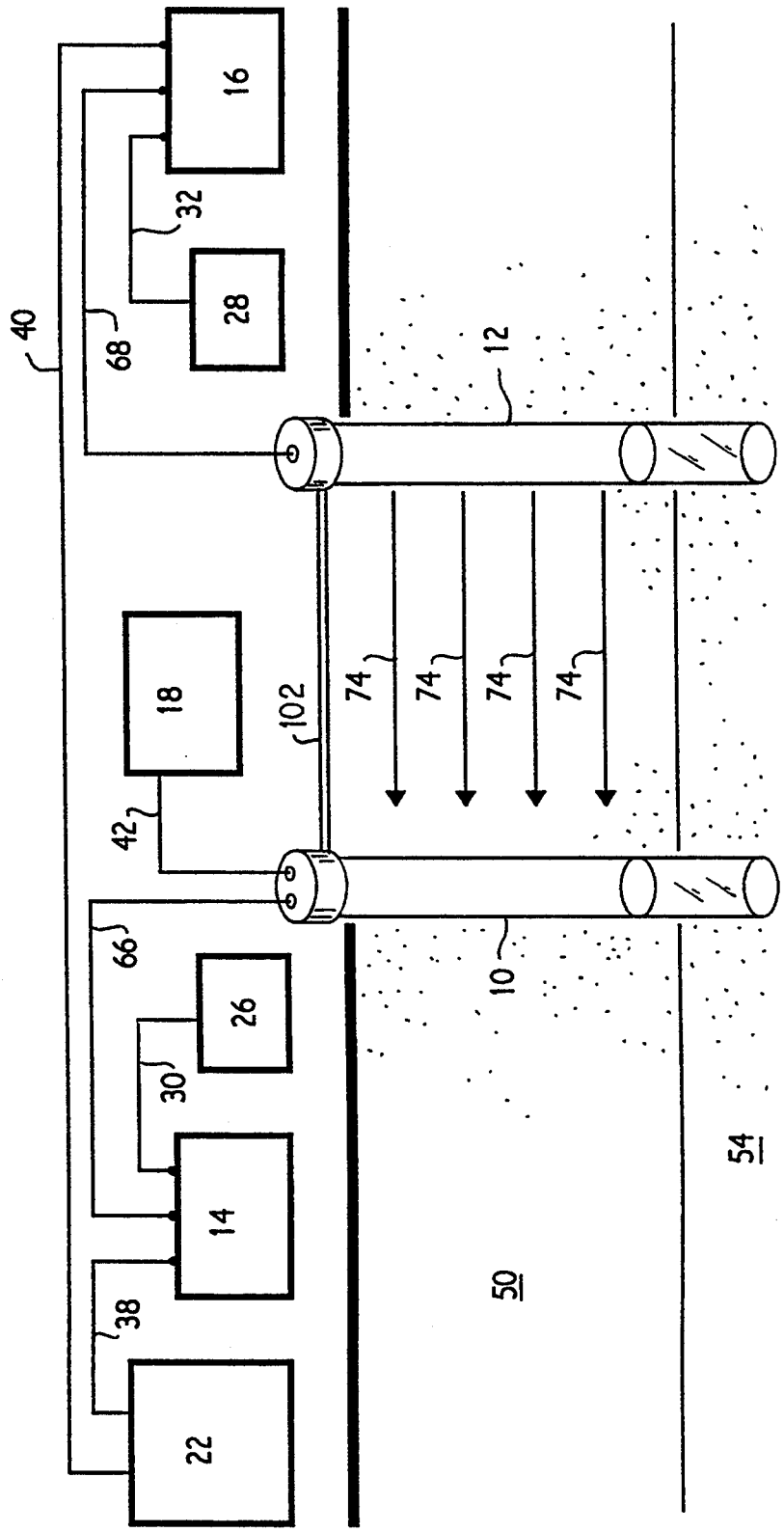
FIG. 6 is a schematic view of the present invention being used to perform a soil permeability test.

FIGS. 5 and 6 illustrate the present invention as used in a soil permeability test. In this embodiment the differential transducer 26 is used to measure the pressure in the upper portion of extraction well 10 and monitoring wells 12 instead of measuring the level of liquid in the wells. Monitoring wells 12 are sealed as is the extraction well. FIG. 5 is a simplified top view of the system showing the positioning of monitoring wells 12 and extraction well 10. The directional lines 74 represent air flow paths through the soil. FIG. 6 illustrates a more detailed view of the typical relationship between extraction well 10 and one of the monitoring wells 12. Extraction well 10 is operatively connected to vacuum system 18. Junction vent box 14 can either be connected directly to vacuum system 18, or, as shown here, to extraction well 10 itself through conduit 66. In either case, the pressure in the upper portion of extraction well 10 will be the same as the pressure in junction vent box 14. This pressure is then applied to the back of differential transducer 26 through transducer cable 30. The front of differential transducer 26 senses the atmospheric pressure in ambient conditions outside of extraction well 10. Data analyzer 22 then receives signals from differential transducer 26 through junction vent box 14 indicative of the difference between atmospheric pressure and the pressure in the upper portion of extraction well 10.

Monitoring well 12 is connected to a junction vent box 16 by conduit 68. The pressure in the upper portion of monitoring well 12 is then applied through junction vent box 16 and transducer cable 32 to the back of differential transducer 28. The front of differential transducer 28 senses atmospheric pressure in ambient conditions outside of the well. Data analyzer 22 then receives signals from differential transducer 28 through junction vent box 16 and cable 40 indicative of the difference between atmospheric pressure and the pressure in the upper portion of the monitoring well.

When vacuum system 18 lowers the pressure in extraction well 10, air will tend to flow along flow path lines 74 from monitoring well 12 to extraction well 10. In order to prevent air from flowing into extraction well 10 from the surface of the soil, the area 102 between extraction well 10 and monitoring wells 12 is typically sealed with a fine clay, such as bentonite. This allows for a better test of the permeability of the soil between the extraction well 10 and monitoring wells 12 since only air from monitoring wells is available to be pulled by vacuum system 18. Therefore, the effect of the pressure drop in extraction well 10 on the pressure in monitoring wells 12 provides an accurate indication of the permeability of the soil between the wells.

Since each differential transducer 14 and 16 measures atmospheric pressure on its front side, the effect of any changes in barometric conditions is negated, and data analyzer 22 can calculate the difference between the pressure in the upper portion of extraction well 10 and monitoring well 12. The pressure difference between the extraction and monitoring well is indicative of the soil's permeability. This test is usually performed prior to a soil vapor extraction procedure. If the soil is not permeable enough, then soil vapor extraction usually will not be effective and other methods are attempted instead.

It is thus believed that the operation and construction of the present invention will be apparent from the foregoing discussion. The method, apparatus, and system shown and described are illustrative examples. It is recognized that various changes and modifications may be made therein without departing from the spirit and scope of the invention as defined by the following claims.

What is claimed is:

1. A pressure sensing system for use with a sealed well containing a liquid comprising:
    means for providing a first desired pressure in the sealed well having the liquid;
    means for supplying said first desired pressure to differential transducer means, said means for supplying including:
    a walled structure which encloses a cavity;
    at least three openings in said walled structure;
    wherein a first of said three openings receives first cable means which has first electrical conductors;
    a second of said three openings receives a second cable means which contains both second electrical conductors and a channel through which gas is able to flow; and
    a third of said three openings receives tubing means through which gas is able to flow;
    wherein said differential transducer means determines the difference between a first sensed pressure and said first desired pressure.

2. The system as recited in claim 1, wherein said first sensed pressure is measured at a point below the surface of the liquid in the sealed well.

3. The system of claim 1, further comprising electrical connectors to operatively interconnect said first electrical conductors to said second electrical conductors.

4. The system as recited in claim 1, further comprising:
- a data analyzer operatively interconnected to said junction vent box device by said first cable means;
- a vacuum system operatively interconnected to the sealed well and said junction vent box by said tubing means;
- wherein said second cable means operatively interconnects said junction vent box device to said differential transducer means.

5. The system as recited in claim 4, wherein said first desired pressure is created in an upper portion of the sealed well through said tubing means and supplied to said differential transducer means through said tubing means, the upper portion of the sealed well, conduit means, said junction vent box device, and said channel of said second cable means by said vacuum system.

6. The system as recited in claim 4, wherein said first desired pressure is created in an upper portion of the sealed well through said tubing means and supplied to said differential transducer means through said tubing means, said junction vent box device, and said channel of said second cable means by said vacuum system.

7. The system as recited in claim 6, wherein said pressure sensing system is used to measure the level of the liquid in the sealed well during a slug test without directly adding any liquid to the sealed well and without extracting any liquid from the sealed well.

8. The system as recited in claim 6, wherein said data analyzer receives electrical signals from said differential transducer means and determines, using said electrical signals, the liquid level in the sealed well.

9. The system as recited in claim 8, further comprising:
- pump means for removing an amount of the liquid from the sealed well dependent on the determined liquid level;
- wherein said pump means is used to maintain a desired liquid level in the sealed well during a soil vapor extraction procedure.

10. The system as recited in claim 6, wherein said second cable means is of sufficient cross-sectional diameter to allow said pressure sensing system to respond to pressure changes in the sealed well rapidly.

11. The system as recited in claim 1, wherein said first and second openings are sealed by a first androgynous connector and a second androgynous connector, respectively, each of which includes a plurality of apertures for receiving at least one of said first and second electrical conductors and one aperture for receiving a channel through which gas is able to flow, and wherein said one aperture in said first androgynous connector for said first opening is plugged, and said one aperture in said second androgynous connector for said second opening is connected to said channel of said second cable means.

12. The system as recited in claim 1, wherein said junction vent box is sufficiently small relative to the size of the sealed well such that gas contained in the cavity of said box does not substantially affect the response of the pressure sensing system.

* * * * *